United States Patent [19]

Hetzel

[11] Patent Number: 5,311,769

[45] Date of Patent: May 17, 1994

[54] METHOD AND APPARATUS FOR AUTOMATIC MEASUREMENT OF EVAPOTRANSPIRATION

[76] Inventor: Henry T. Hetzel, 1931 S. County Rd. 19, Loveland, Colo. 80537

[21] Appl. No.: 845,611

[22] Filed: Mar. 4, 1992

[51] Int. Cl.⁵ ............................................. G01N 33/18
[52] U.S. Cl. ..................................................... 73/61.77
[58] Field of Search .................... 73/866.4, 198, 223, 73/224, 61.77; 137/391, 392, 395, 396; 392/386, 394, 400, 402, 403, 325, 327, 322; 261/154, DIG. 65

[56] References Cited

U.S. PATENT DOCUMENTS

| | | | |
|---|---|---|---|
| 2,505,905 | 5/1950 | McAfee | 73/223 |
| 2,625,933 | 1/1953 | Salisbury | 73/223 |
| 3,759,286 | 9/1973 | Page | 137/392 |
| 3,774,185 | 11/1973 | Parth | 137/392 |
| 4,002,996 | 1/1977 | Klebanoff et al. | 137/392 |
| 4,418,576 | 12/1983 | White | 73/61.77 |
| 4,952,779 | 8/1990 | Eaton-Williams | 392/327 |

*Primary Examiner*—Robert Raevis
*Attorney, Agent, or Firm*—Edward L. Miller

[57] ABSTRACT

An automatic atmometer includes an evaporating head that is coupled to a metering vial through a three-way valve controlled by fluid sensors disposed proximate inlet and open ends of the metering vial. The three-way valve is ordinarily in a quiescent state that connects the evaporating head to the metering vial. As water evaporates from the evaporating head water is drawn by suction out of the metering vial. When a sensor proximate the inlet of the metering vial indicates that the vial is empty the three-way valve is activated. This refills the metering vial from a fluid reservoir above the metering vial. As soon as one or more sensors proximate the open end of the metering vial indicate that the vial is full the three-way valve is returned to its quiescent condition. An output signal activates a counter or other logging device to record the number of times the metering vial has been emptied and refilled. Fluid presence at various portions of the metering vial is sensed by capacitive structures each producing a varying amount of capacitance according to the presence or absence of the fluid. The amount of an RF signal coupled through each sensor is measured and compared to a reference voltage. The reference voltage is itself produced from a similar capacitive structure so that the measured voltage and the reference voltage have the same temperature coefficient.

15 Claims, 4 Drawing Sheets

FLUID IS PRESENT

NO FLUID IS PRESENT

METHOD AND APPARATUS FOR AUTOMATIC MEASUREMENT OF EVAPOTRANSPIRATION

REFERENCE TO ISSUED PATENT

This Patent Application describes improvements to the subject matter disclosed in issued U.S. Pat. No. 4,709,585 which issued Dec. 1, 1987 to Jonathan M. Altenhofen, U.S. Pat. No. 4,709,585 is hereby incorporated by reference.

BACKGROUND AND SUMMARY OF THE INVENTION

The subject matter described herein pertains to the automatic measurement of the evaporation of water from a surface that mimics the albedo and diffusion resistance to water vapor of the leaf of a plant. As a class, devices of this sort are called atmometers. The instant device whose method and apparatus are disclosed may be termed an automatic atmometer.

Prior art atmometers have to be read manually, generally by making visual note of the fluid level against a sight gauge. This is both bothersome and error prone. It would be desirable if the readings could be taken electronically, even in the absence of an observer, and with a degree of accuracy exceeding that afforded by sight gauges.

These objectives are achieved in an automatic atmometer whose evaporating head draws its fluid through a three-way valve whose quiescent position connects the evaporating head to one end of a metering vial equipped with fluid level sensors indicating "full" and "empty". The fluid metering vial is open to the atmosphere at its other end. The difference in volume contained by the metering vial when full and when empty is its displacement. The displacement is selected to be fairly small, say, a milliliter.

Evaporation of water at the evaporating head draws water by suction out of the metering vial. When the sensors indicate that the vial is empty the three-way valve is activated. This blocks the connection to the evaporating head and (temporarily) connects the metering vial to a fluid reservoir located above it. Gravity flow refills the metering vial until the sensors indicate that it is full. At that time the three-way valve is returned to its quiescent condition.

Each refilling of the metering vial indicates that an amount of water equal to the displacement of the metering vial has been evaporated. The circuit that controls the switching of the three-way valve also produces an output indicative of that switching. That output can be used to increment or otherwise signal a recording or other data logging device.

The subject matter disclosed herein also pertains to a method and apparatus for the measurement of fluid flow with a metering vial equipped with capacitive sensors to detect the presence and absence of fluid at various places along the vial. The metering vial is intended to function reliably in environments where high surface tension and the possibility of condensation combine to produce the possibility that droplets of condensation might be sucked back up into a distal end of the vial open to the atmosphere. It is desirable for the method and apparatus for measuring fluid flow to work with equal accuracy for fairly rapid flows, as well as for flow rates that are almost zero.

These objectives are met by a metering vial having an inlet end below an expansion chamber, above which is a U-shaped siphon extending downwards on the other end by a convenient amount. A fluid detector is located proximate the inlet, while two fluid detectors are located some distance apart along the downward extending leg of the siphon leading to the opening to the atmosphere. The inlet fluid sensor detects, by the absence of fluid, that the metering vial is empty. The other two fluid sensors, by their simultaneously detecting the presence of fluid, indicate that the vial is full. A logic circuit controls whatever response is desired to these detected conditions.

The expansion chamber has a volume exceeding that portion of the metering vial that is between the two fluid sensors that cooperate to indicate the full-of-fluid condition. This volume relationship property, in conjunction with the logical AND'ing of the outputs of those two sensors, operates to produce immunity to the problem of condensation and surface tension. This is achieved by avoiding a false full indication that might occur if a drop of condensation were sucked into the open end of the metering vial as the vial's displacement is drawn out the inlet end.

Each capacitive fluid sensor includes a driving plate and a driven plate, separated by a grounded shield. Each plate is essentially a cylinder around a section of glass tubing that is part of the metering vial. The shield is a metal plate with a hole therein to allow passage therethrough of the glass tube. The driving plate is connected to the output of a high level radio frequency oscillator. The amount of signal coupled through the capacitor varies greatly according to the dielectric constants of the material between the plates. When there is no fluid present there is only the relatively low dielectric constants of the glass tubing and the air therein. The shield blocks direct ("line of sight") coupling between the plates. However, when there is fluid in the tube the dielectric constant is increased, and a greater signal is coupled into the driven plate. The signal at the driven plate is rectified and compared to a reference voltage to produce a logic signal indicative of the presence or absence of the fluid.

The reference voltage is produced from another capacitor constructed in the same general fashion as those for the sensors. This gives the reference voltage the same temperature coefficient as the sensors.

DESCRIPTION OF A PREFERRED EMBODIMENT

Figure 1:
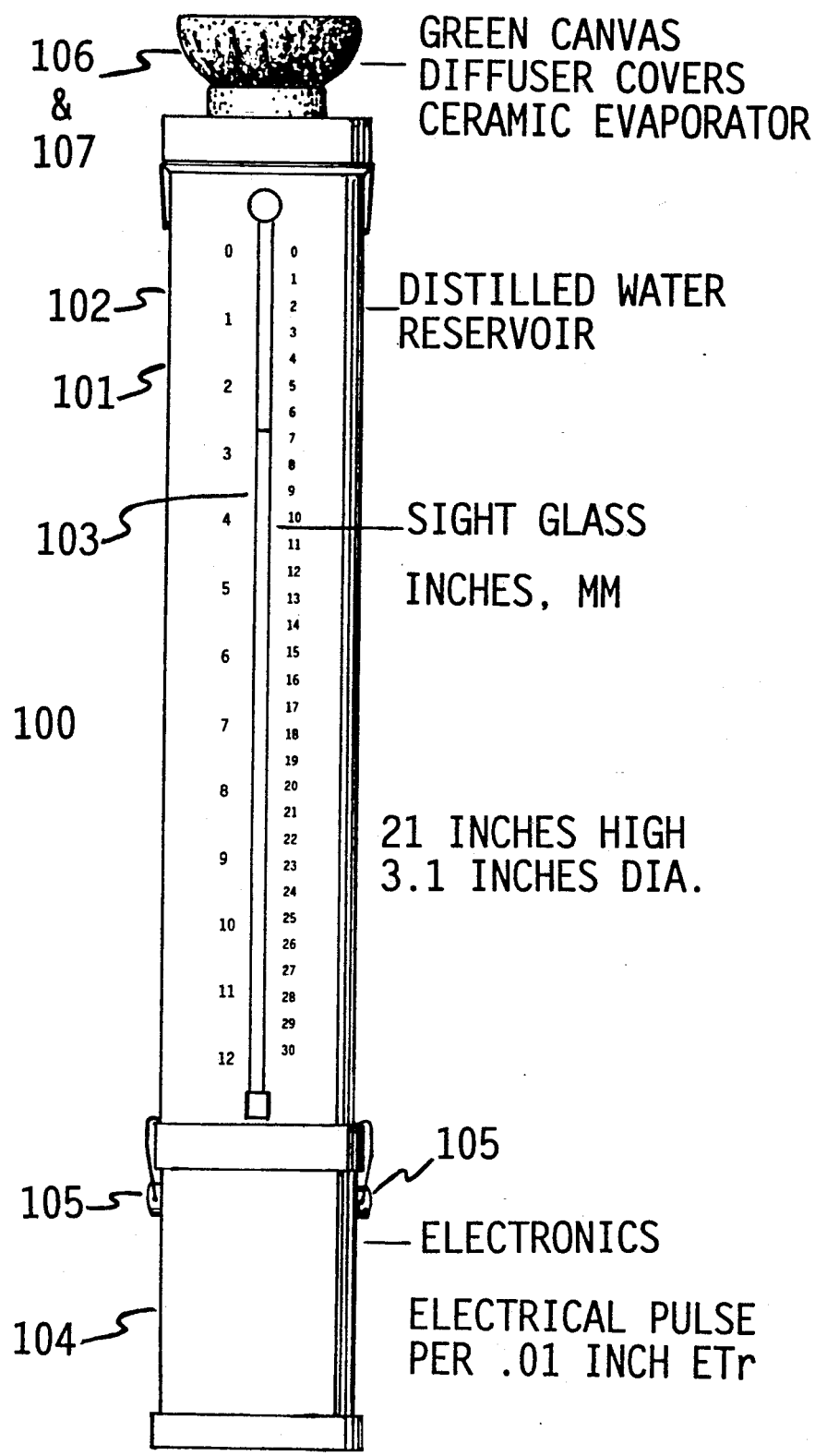
FIG. 1 is a front view of an automatic atmometer constructed in accordance with the invention.

FIG. 1 is a front view of an apparatus 100 for automatic measurement of evapotranspiration, or automatic atmometer. The particular apparatus depicted 100 is an automatic atmometer intended for agricultrual uses where the evaporation of water is to be measured and recorded. It is of generally cylindrical shape with a diameter of 3.1 inches and a length of 21 inches.

The automatic atmometer 100 includes a cylindrical housing/reservoir 102 which both provides mechanical support for various other elements and holds the fluid whose evaporation is to be measured. Along one side of the reservoir 102 is a fluid level sight gauge 101 to allow manual recording of the fluid level, if desired, but which is principally for ensuring that the fluid level within is adequate for continued operation. Adjacent the fluid level sight gauge 101 is a scale 103 marked in both inches and millimeters.

At the top of the automatic atmometer 100 is a fluid evaporating head 106 constructed of ceramic material, as is known from U.S. Pat. No. 4,709,585. Complete fluid evaporating heads may be obtained from the C&M Meteorological Co. in Riverside, Calif. As shown in FIG. 1 the fluid evaporating head 106 is (completely) covered with a (green) canvas membrane 107 that simulates the albedo and diffusion resistance (to water vapor) of the (green) leaf of a plant. Canvas membranes 107 of other colors may be useful for other types of plants. Likewise, evaporating surfaces other than the ceramic fluid evaporating head 106 may be useful, including, but not limited to, free water surfaces.

At the bottom of the atmometer 100 is a cover 104 held in place by latches 105. Within the cover 104 is the automatic portion of the automatic atmometer 100.

In agricultural operation, the automatic atmometer 100 is filled with water, primed, placed upright in the location (e.g., a field) where the evapotranspiration is to be measured, and the recording device(s) attached and initialized.

Figure 2:
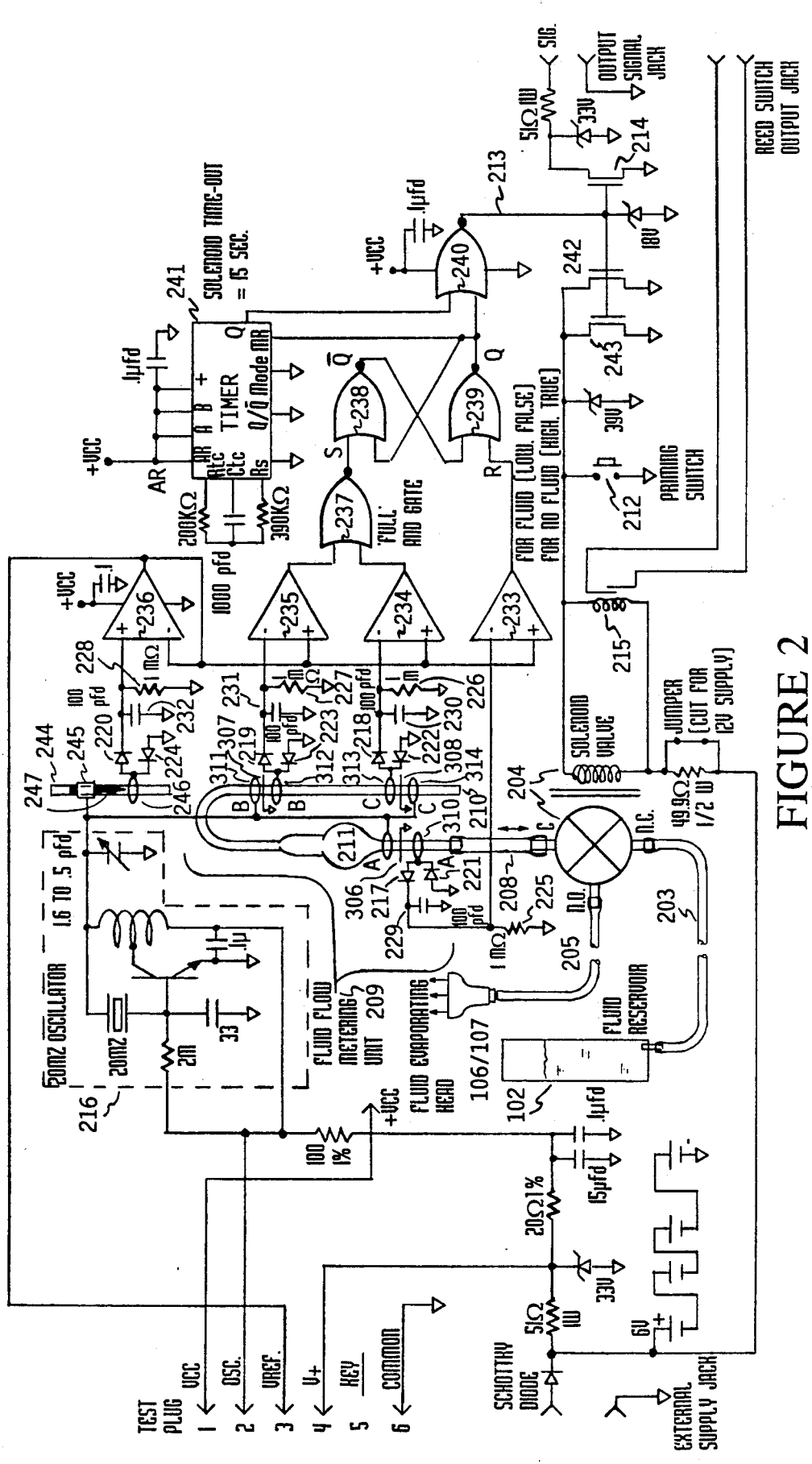
FIG. 2 is a schematic diagram of a circuit within the automatic atmometer of FIG. 1.

Refer now to FIG. 2, wherein is shown a combined block diagram 201 of a fluid flow path with a schematic of the controlling circuitry in the apparatus 100 for automatic measurement of evapotranspiration (for brevity, hereinafter referred to as simply an "automatic atmometer").

In particular, note that a porcelain evaporating head 106, covered by membrane 107, is connected by tubing 205 to a "three-way" solenoid valve 204. Also connected to solenoid valve 204 is a fluid reservoir 102 (connected by a passage or tube 203) and a fluid flow metering unit 209 (connected by tubing 208). The normal quiescient, or unactivated, state of solenoid valve 204 is to connect, or provide unobstructed passage between, tubes 205 and 208, while blocking passage or tube 203. This quiescent state connects the fluid flow metering unit 209 to the evaporating head 106, while at the same time prevents fluid from leaving the fluid reservoir 102. (Of course, in the terrestrial atmospheric environment of agriculture that fluid is water. It will be appreciated that in other environments the evaporation of another fluid might be measured.)

During the time that solenoid valve 204 is in its normal quiescient state, fluid flow metering unit 209 itself acts as a reservoir to supply fluid for evaporation to evaporating head 106. The evaporation of the fluid acts like a pump, with atmospheric pressure forcing the fluid in the fluid flow metering unit 209 out of the fluid flow metering unit 209, through tubes 208 and 205 and into the evaporating head 106. The fluid flow metering unit 209 has a certain capacity, and sensors to detect when it is "full" and when it is "empty". Actually, the terms "full" and "empty" do not refer to the ultimate physical ability of the fluid flow metering unit 209 to hold fluid; they represent a lesser range corresponding to the displacement of a known amount of fluid, say, about a milli-liter. That known amount of fluid is selected to measure, with a desired degree of precision, the amount of evapoprated fluid over some time period of interest, say, twenty-four hours or two weeks.

To this end, it will be appreciated that when the sensors (to be described later on below) indicate that the fluid flow metering unit 209 is "empty", solenoid value 204 is activated. In its activated state it provides connection, or unobstruced passage, between the fluid reservoir 102 and the fluid flow metering unit 209, while at the same time blocking fluid flow in or out of tubing 205. This action allows fluid flow metering unit 209 to be refilled (by gravity flow) from the fluid reservoir 102, which refilling continues until the sensors indicate "full". At that time solenoid valve 204 returns to its normal quiescient state, and evaporating continues, again using fluid from the now newly refilled fluid flow metering unit 209.

Fluid evaporation at the fluid evaporation head 106 continues undisturbed even during the time the solenoid valve 204 is activated (which ranges from about 1.6 sec to 3.0 sec). If it were the case that replenishment of the supply of fluid to the evaporating head 106 were prevented altogether by an activated solenoid valve 204 in conjunction with a completely rigid length of tubing 205, that situation could, in principle, somewhat "starve" the evaporating head 106 and result in spuriously reduced evaporation. While this would ordinarily be an extremely small error (unless the evaporation rate were large and the refill times long—an unlikely combination), it would nevertheless be an error. The present automatic automater 100 is easily capable of accuracies of 1/10% or better, and avoidance of this source of error is felt to be superior over simply ignoring it. The error is easily avoided by ensuring that tubing 205 is flexible or elastic, so that it will readily contract as needed to supply fluid for continued unimpeded evaporation. To this end, as well as for convenience in the priming operation described below, a longer than absolutely necessary length of PVC or surgical tubing is preferred for tubing 205.

On the other hand, a ceramic fluid evaporating head 106 of the type described herein can actually produce in water-filled supply tube 205 a partial vacuum that is limited principally only by the vapor pressure of water. Given this robust degree of suction and the short time required by the fluid flow metering unit 209 to cycle, even the slightest compliance in the supply tube 205 is sufficient to prevent any discernable "starvation" while the solenoid valve 204 is active.

It is now apparent that the rate of fluid evaporation from the combination of the evaporating head 106 and membrane 107 is indicated by the rate at which the fluid flow metering unit 209 is emptied and refilled. It follows immediately that the amount of fluid evaporated over any time period of interest is simply the number of such refillings during that period multiplied by the displacement representing the difference between "full" and "empty". To provide for automatic registering of evaporation rate or for accumulation of total evaporation, the signal 213 that drives solenoid valve 204 is buffered and made available for use as either a momentarily conducting transistor 214 or a momentary excursion in the contacts of a relay 215. These constitute the "output" of the automatic atmometer 100, and may be connected to any suitable recording device, such as an impulse counter, data logger, or a suitable integrator coupled to a chart recorder.

Before turning to a discussion of the particular nature of the sensors in the fluid flow metering unit 209 and the circuitry that is associated therewith, certain general properties of the fluid flow metering unit 209 should be pointed out. First, its displacement (the difference between "full" and "empty") is fairly small, since evaporation in an (agricultural) atmometer is generally regarded as a process imperceptible over short periods of time, say, a quarter of an hour. In a preferred embodiment for agricultural use, a displacement of about 1 ml has been found satisfactory. The actual displacement is adjusted during calibration so that one refilling of the fluid flow metering unit 209 corresponds to one minor graduation (say, 0.01 inch or 0.1 mm) on the scale 103 for the sight gauge 101 for the automatic atmometer 100. In this way the electrical output signal can easily be directly utilized without the need for a conversion of units. For example, an impulse counter (not shown) incremented by the buffered solenoid drive signal (214, 215) would read directly as DD.DD inches or DD.D mm simply by correctly locating the decimal point in the display of that impulse counter.

To continue with the general properties of the fluid flow metering unit 209, a distant end 210 of the fluid flow metering unit 209 is open to the atmosphere. This is necessary for atmospheric pressure to provide the force that pushes fluid up into the evaporating head 106 as fluid evaporates, as already described. It also cooperates with a convenient way to initially fill, or prime, the fluid flow metering unit 209. Such priming is accomplished by the simple expedient of manually pressing a pushbutton switch 212 (that activates the solenoid valve 204) until bubble free fluid flows from the open end 210.

As will be discussed in greater detail below, there are three fluid sensors associated with the fluid flow metering unit 209. Let these be designated A, B and C. As can be seen in the figure, the fluid flow metering unit 209 is essentially a long narrow path, conveniently, although not necessarily, of glass, within which the fluid to be measured can flow back and forth. One end of this path is connected to the solenoid valve 204 via tube 208, with the opening 210 at the other end of the path. Let the end connected to tube 208 be called the active end, and the end with the opening 210 be called the open end. Sensor A is located proximate the active end, while sensor C is proximate the open end. Sensor B is disposed along the length of the fluid path within the fluid flow metering unit 209, and inbetween sensors A and B. An expansion chamber 211 exists as part of the fluid flow path between sensor A and sensor B.

In broad general terms, sensor A is used to detect the "empty" condition, while senors B and C are combined to produce and indication of the "full" condition.

The expansion chamber 211 cooperates with the combination of sensors B and C, and is a precaution against inaccurate operation caused by inappropriate inclusion of stray fluid into a portion of the fluid flow path at a time when it should contain only air. (When this happens it looks as if a "large bubble" has formed. Although convenient, such terminology is misleading, however, since it implies that it is the trapped air that shouldn't be there. Actually, it is the other way around; the air belongs there, but some of the fluid does not.) This "large bubble" phenomenon is thought to be quite infrequent in practice, although it can be readily "forced" to occur through deliberate actions that are probably very seldom, if ever, representative of actual field conditions. Nevertheless, in the spirit of bullet proofing whenever it is possible to do so, the expansion chamber 211 (and the use of two sensors B and C, in place of C alone) have been incorporated in the automatic atmometer 100. Their function is described in the next paragraphs, and in further detail in a later section dealing with sensors B and C.

It appears that condensation can sometimes form a droplet on the outside of open end 210. It is thought that during normal evaporation at evaporating head 106 the receeding of the fluid away from the open end 210 might suck the droplet in behind it, trapping some air and creating a "large bubble". The problem that such a "large bubble" presents is that it can fool the sensors, resulting in erratic operation until the "large bubble" is somehow cleared.

The principal purpose of the expansion chamber 211 is to either: (a) "break" any such "large bubbles" by collecting the offending water drop into other water that is where it is supposed to be; or else (b), assist in the expulsion of any plug of water (the sucked-in drop) forming the "down stream end" of a large region of air trapped in a region of the fluid flow metering unit 209 adjacent sensors B and C.

Small bubbles have not been observed in the instant agricultural automatic atmometer 100, although this observed absence is not a guarantee. However, it should be noted that even if they should occur, small bubbles will not cause malfunctions. The principal cause of small bubbles would appear to be coalescing of dissolved gasses in the fluid during a rise in temperature. Small bubbles would either stick to the wall of the tubing while the fluid flows around them, or they would flow along with the fluid. They would cause a very small error in recorded fluid flow, owing to their displacement. But this error would be quite negligible, and in any event, probably unavoidable.

The basic cycle of metering operation, then, is this: First, the fluid reservoir 102 is filled. Then the solenoid valve 204 is activated until bubble free fluid has completely filled the fluid flow metering unit 209. Also, steps are taken to prime the fluid path from solenoid valve 204 to the evaporating head 106. Then, as evaporation proceeds the fluid in the fluid flow metering unit 209 receeds from the open end toward sensor C, eventually passing it and continuing to receed toward sensors B and then A. When the condition of sensor A reports "empty" neither of sensors B or C will be reporting the presence of fluid, either. This state of affairs is detected by logic circuitry to be described below, and results in the activation of the solenoid valve 204. With the activation of the solenoid valve 204, fluid enters the fluid flow metering unit 209 from its active end, via tube 208. First sensor A, and then also sensor B followed by sensor C, will report the presence of fluid. When both sensors B and C report the presence of fluid the logic circuitry returns the solenoid valve 204 to its normal unactivated state.

The astute observer will note that the volume of fluid corresponding to the distance between the opening 210 in the open end and sensor C is not correctly accounted for, as that extra volume is part of the first cycle, but not the others. The size of the error depends upon the distance between sensor C and the opening 210, as well as how far the fluid overshoots past sensor C during a refill. In practice, the distance between the opening 210 and sensor C is small, and there is not any appreciable overshoot. The resulting error is really quite small (a drop or two of water at the most) and soon fades into insignificance once any appreciable evaporation has occurred. In any event, the error is entirely avoidable by the simple and desirable expedient of allowing the automatic atmometer 100 to operate for a few cycles of the fluid flow metering unit 209 before reseting or noting the starting setting of the recording device.

In a preferred embodiment the time required to fill the fluid flow metering unit 209 with water varies from about 1.6 sec when the reservoir 102 is full, to about 3 sec when the reservoir 102 is low. The preferred solenoid valve 204 draws only about 650 milliwatts when active. In addition, the power required to run an oscillator used in sensing fluid level (as discussed below) has been minimized. As a result, the preferred circuit disclosed herein will run in an agricultrual atmometer for about six months on four alkaline AA cells.

In a preferred embodiment the fluid flow metering unit 209 has a particular orientation with respect to gravity, in that the longitudinal axis of the expansion chamber 211 is vertical. In a particular preferred embodiment, the portion of the fluid flow metering unit 209 that extends from sensor B to opening 210 is also vertical, although that is merely a convenience, and not absolutely necessary for proper operation. Likewise, the path of drops of fluid falling from opening 210 is kept free of circuitry and anything else adversely affected by the fluid expelled during the priming operation. More will be said about the structure of the fluid flow metering unit 209 during the discussion for FIG. 3. For now, these points are worth noting: The shape of the particular expansion chamber 211 shown in FIG. 2 requires a vertical axis. Smooth transitions in the inside diameter seem to be important, since abrupt changes in diameter produce either steps or overhangs. Each of these might collect fillets of fluid (especially if the fluid is water!) that, in turn, might interfere with reliable "bubble bursting". It will be appreciated that there may be other structures that can be substituted for expansion chamber 211, and that those other structures might not require a vertical or other particular orientation.

Here is how the automatic atmometer 100 is primed upon being initially put into service. Fluid evaporating head 106 is removed from atop fluid reservoir 102. This exposes the interior of the reservoir 102, so that it may be filled with fluid. After it is filled switch 212 is pressed to activate solenoid valve 204 until bubble-free fluid flow from the open end 210 of the fluid flow metering unit 209. Next, the fluid evaporating head 106 is detached from tube 205. (The underside of fluid evaporating head 106—not shown—has an opening that receives a one-hole rubber stopper having a short piece of glass tubing extending through the hole. The short piece of glass tubing serves as a nipple onto which tubing 205 attaches.) The fluid evaporating head 106 is then turned upside down and the rubber stopper removed while fluid is poured into the fluid evaporating head 106. After replacing the rubber stopper, a collapsed syringe (less the needle) is connected to the free end of tube 205, and the plunger withdrawn to pull fluid up through tube 205 until the tube 205 is full of fluid. At that point a compression tubing clamp is applied to the tube 205 and the syringe removed. Now the fluid evaporating surface is topped off, and if necessary the end of tube 205 as well, whereupon the tube 205 is re-attached to the nipple. Because the diameter of the tube 205 (and hence, of the nipple also) is small, say on the order of 1/16 to ⅛ inch, surface tension is sufficient to prevent the loss of fluid and the inclusion of any significant bubbles during the reattachment. The compression clamp may now be removed and the fluid evaporating surface remounted atop the reservoir 102. After reseting the recording device or noting its initial value, the automatic atmometer 100 is ready to be placed into service.

It will be noted that it is not necessary to perform the priming steps outlined above merely to refill the reservoir 102. Such refilling may be done without removing the automatic atmometer 100 from service. All that is needed is to lift away the fluid evaporating head 106 and refill the reservoir with fluid. Then the fluid evaporating head 106 is replaced, and normal operation continues uninterrupted.

Figure 3:
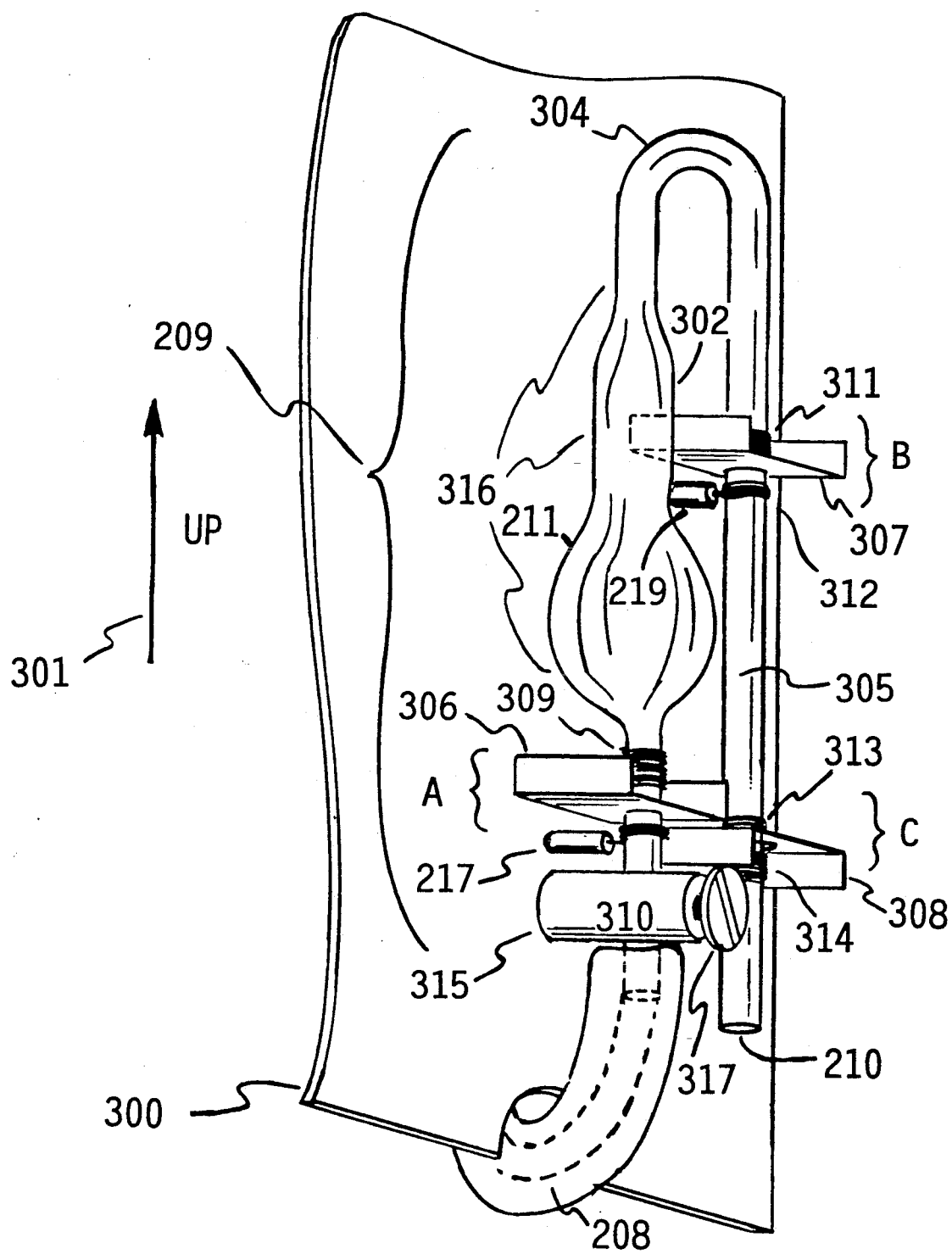
FIG. 3 is a perspective view of a fluid flow metering unit used in connection with the schematic of FIG. 2.

Refer now to FIG. 3, where is shown a perspective view of the fluid flow metering unit 209, mounted upon a printed circuit board 300 (only a part of which is shown) that also carries the control circuit 201 of FIG. 2. The printed circuit board 300 is mounted vertically, such that arrow 301 indicates the upward direction. A vial portion 316 of the fluid flow metering unit 209 is fabricated of glass. The vial portion 316 includes expansion chamber 211, neck 302, siphon 304 and separation section 305. The open end 210 of fluid flow metering unit 209 is at a distal end of separation section 305. The active end of fluid flow metering unit 209 is somewhat below the expansion chamber 211, by the length of a short run of tubing, and is attached to tube 208 after passing through a support post 315.

The glass vial 316 is also supported by three brass shields 306, 307 and 308. Each of these shields has a hole to allow passage of the glass therethrough, and each shield is soldered to a ground plane on the printed circuit board. The importance of the shields in the operation of the sensors is described in connection with FIG. 4.

The outer diameter of the smaller diameter glass tubing is about 0.120", while the inside diameter thereof is about 0.072". The overall length of the glass portion is about 2.25" from the open end 210 to the top of the outer surface of the bend in the siphon 304. The greatest diameter of the expansion chamber 211 is about 0.400", while its height in the vertical direction is about 0.500". The greatest outside diameter of the neck portion 302 is about 0.220", while its height is about 0.500". The radius of the bend in the siphon 304 is about 0.200", and the length of the short section of tubing below the expansion chamber 211 (the far end of which is the active end) is about 0.750".

Besides helping support the glass portion of the fluid flow metering unit 209, shields 306, 307 and 308 cooperate in the operation of the fluid level sensors A, B and C, respectively. Each sensor includes a shield and two plates of a capacitor. Of the two plates, one is a driving plate, while the other is a driven plate. There is an interior length of about 0.110" between the plates. The shield is located about in the middle of the 0.110" length. The driving plates are each formed of four close wound turns of 22 AWG tinned solid copper wire, wound so as to have a slip fit over the glass tubing. The shank of a #31 drill bit works well as a mandrel for this purpose. The driven plates of the capacitive sensors A, B and C are formed similarly, but from two turns of the lead of a low capacitance diode. A minimum amount of length occurs between the two turns and the body of the diode, the other lead of which enters a hole in the printed circuit board 300. All of the four-turn and two-turn plates of the capacitive sensors A, B and C may be lightly soldered to themselves to assist in shape retention in the event the glass vial 316 is even replaced. In that connection, note that the glass vial 316 can indeed be inserted and removed from the shield and capacitive sensor plates described in this paragraph.

Solenoid valve 204 is located on the other side of the printed circuit board 300, so that tubing 208 is a relatively short U-shaped bend. A nylon screw 317 in support post 315 bears against the glass vial 316 through an intervening vinyl friction pad, and in conjunction with the support afforded by the holes in the shields 306, 307 and 308, retains the glass vial 316 in position. The glass vial 316 has calibration marks (not shown) opposite the locations of the shields for sensors A and C, such that when it is installed so that the marks line up with the shields the displacement of the resulting fluid flow metering unit 209 is of the desired amount. In other words, loosening the set screw 317 in support post 315 and then sliding the glass vial 316 up or down is how the displacement of the fluid flow metering unit 209 is adjusted. Sliding the siphon 304 toward support post 315 decreases the displacement, while sliding it away increases displacement.

The driving plates of the sensors A, B and C are each connected to the output of a high level 20 MHz oscillator. The shield between a driving plate and its driven plate prevents capacitive coupling therebetween except through the hole in the shield, which is to say, through the glass and its contents. Those contents are either air or fluid. In the case where the fluid is distilled water the dielectric constant of the fluid at 20 MHz is many times that of air (about seventy-eight times!). The result is that there is a significantly greater coupling between the driving and driven plates when there is fluid in the region of the tubing spanned by a sensor, compared to when there is no fluid. The diode rectifies the coupled signal, after which the detected level is conditioned to produce a logic signal indicative of the presence or absence of fluid at that sensor.

Figure 4B:
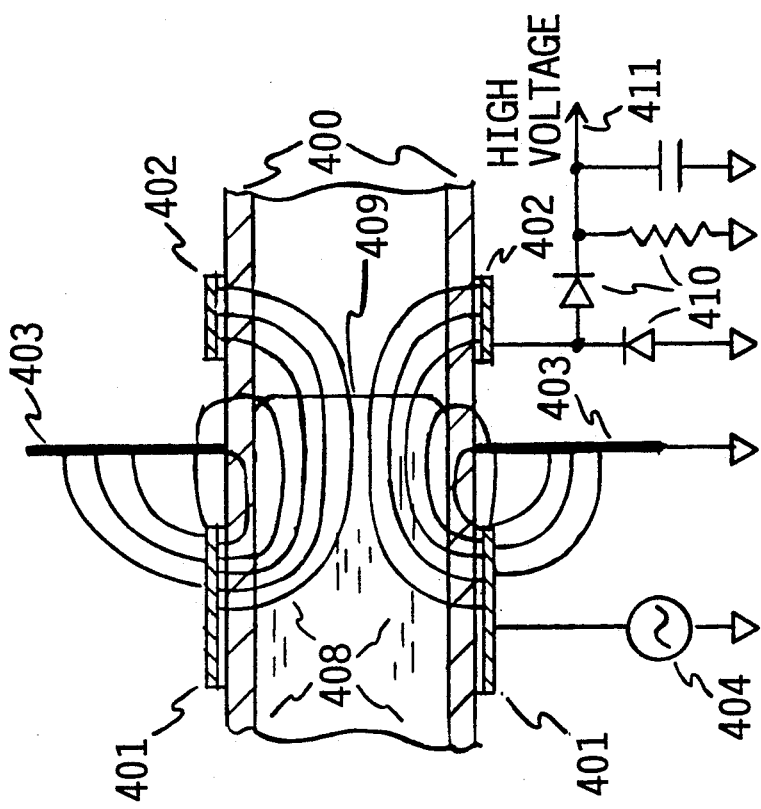
FIGS. 4A and 4B are diagrams illustrating how electrostatic fields behave within the capacitive fluid level sensors of FIGS. 2 and 3.
Figure 4A:
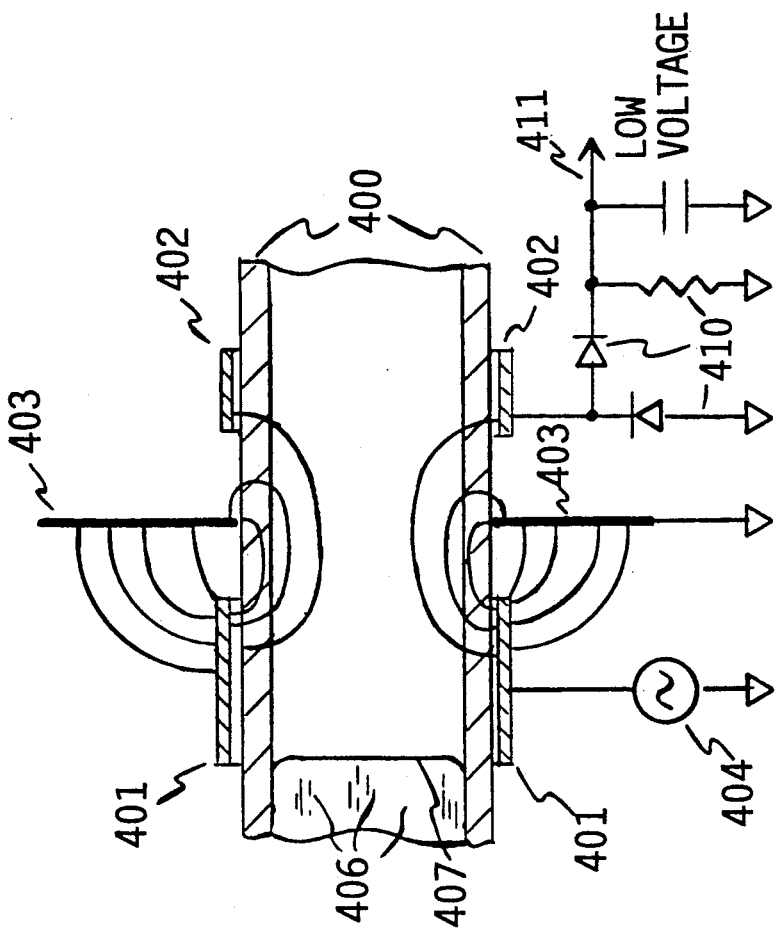

Refer now to FIGS. 4A and 4B, and consider the operation of the fluid sensors A, B and C. In each part of the figure the same capacitive sensing structure is shown. The only difference is where the fluid is relative to the elements of the capacitor. Those elements include glass tubing 400 within which fluid (406, 408) flows. The capacitor is made up of a driving plate 401 in the form of an annular ring fitting closely over the glass tube 400. A short distance away from the driving plate 401 is a driven plate 402, also in the form of a close fitting annular ring. Disposed between the driving plate 401 and the driven plate 402 is an electrostatic shield 403. Its physical form is that of a metal plate having a hole therein for the glass tube 400 to pass through. Finally, note the radio frequency oscillator 404 that supplies a signal to driving plate 401, and the signal level detection circuitry 410 coupled to the driven plate 402. This circuitry produces an output signal 411 whose level is principally a function of whether or not there is fluid (406, 408) proximate the shield 403.

Suppose the fluid 406 is located as shown in FIG. 4A. Its meniscus 407 is well to the left of shield 403. As a result, there is no particularly good path for the lines of electrostatic force to extend between the two plates 401 and 402. Some lines of force extend between driving plate 401 and the shield 403. This happens in both figures, and is of no particular interest. Of greater interest is the extent to which the lines of force penetrate into the glass 400, penetrate all the way through the glass, and where they then go.

Now, pyrex glass has a dielectric constant of about 4.8, which is significantly better than air, at one. Accordingly, the lines of electrostatic force find it somewhat easier to enter the glass 400 and travel through it. However, the first terminus they pass is the shield 403, and it is a good one, since it is grounded directly and is in close proximity to the glass. Thus, the shield 403 effectively terminates any lines of electrostatic force traveling through the glass 400, so that almost none will continue on through the glass 400 to reach the driven plate 402. Some lines of electrostatic force will pass completely through the glass 400 into the interior portion of the tube, and will either terminate at the shield 403 or at the driven plate 402. Not many make it to the driven plate 402, however, and remember that the dielectric constant of the interior of the tube (one, since it is air) is less than that of the glass itself. So, the level of the detected signal 411 is quite low, say, on the order of 50 mv for an 8 VRMS drive from oscillator 404.

Now refer to FIG. 4B and suppose that fluid 408 has advanced so that its meniscus 409 extends just beyond the plane of the shield 403. Now the situation is entirely different. The lines of electrostatic force prefer to penetrate all the way through the glass 400 and into the extremely high dielectric constant of the fluid 408. Once into the fluid 408 it is fairly easy to extend from meniscus 409 over to the driven plate 402. This substantially raises the capacitance between the driving and driven plates, and greatly increases the level of output signal 411 (to about 900 mv) for all positions of meniscus 409 at or to the right of the location shown in FIG. 4B.

It can now be appreciated that the shield 403 plays an important role in the operation of the capacitive sensors A, B and C. If it were not there, it would be reasonable to expect the change in capacitance to vary as a more nearly linear function of the movement of fluid between the driving plate 401 and the driven plate 402. This would produce a gradual change in the output voltage 411, which degrades the accuracy of the measurement of the displacement of fluid within the vial 316, since it raises the volume uncertainty associated with crossing a given threshold in output voltage 411. But with the presence of the shield there is a very abrupt knee in the function describing the relationship between fluid position and the output signal 411. It is the shield that allows the automatic atmometer 100 to exhibit accuracies of one tenth of a percent, or better!

Refer again to FIG. 2, and note that a 20 MHz oscillator 216 is connected to the driving plates 309, 311 and 314 of sensing the capacitors in sensors A, B and C, respectively. The 20 MHz oscillator 216 produces about an eight volt RMS signal. The 20 MHz oscillator 216 has been optimized to produce a large signal, while at the same time drawing as little power as practical. It is essential that the tank circuit have a fairly high Q. In connection with this, the inductance of that tank is as large as possible, with almost all of the resonating capacitance being distributed among the capactive sensors A, B and C and the various stray capacitances in the traces of the printed circuit board 300.

Consider sensor A. Diode 217 rectifies positive half-cycles of any of the 20 MHz signal coupled from driving plate 310 to driven plate 309. These are developed across resistor 225 as a positive voltage to ground, which are then filtered by capacitor 229. Diode 221 provides a return path for negative half-cycles. The detected positive voltage is on the order of 50 mv when there is no fluid present, and on the order of 900 mv when fluid is present. The detected positive voltage is applied to the inverting input of a comparator 233. The output of the comparator 233 is near ground when fluid is present at sensor A, and near +6 V when there is no fluid present at sensor A. Sensors B and C are connected in like fashion to comparators 235 and 234, respectively.

The non-inverting input of each of the comparators 233, 234 and 235 is coupled to the output of a unity gain buffer 236. The input of the unity gain buffer 236 is derived from another detector network of diodes 220, 224, resistor 228 and capacitor 232, just as for the three comparators 233, 234 and 235. And as before, the diode 220 and resistor 228 develop a positive voltage from a capacitor formed on a separate length of glass tubing 244. As far as the glass tubing 244, the driving plate 245 and the driven plate 246 are concerned, these are all of identical construction to the three sensor capacitors A, B and C. However, there is no shield, and an adjustable tapered conductive slug 247 inside tube 244 takes the place of the fluid. The slug is cemented in a position that produces an output voltage from unity gain buffer 236 which is half-way between the no fluid and full-of-fluid conditions at the inverting inputs of the comparators 233, 234 and 235; i.e., around +500 mv. This serves as the threshold voltage against which the comparators compare the detected positive voltage from their respective sensors. The threshold voltage is derived in this fashion (i.e., in the same general way as the fluid level voltages are produced) so that any temperature coefficient for the detected positive voltages for the sensors A, B and C will be balanced by a like temperature coefficient for the threshold voltage.

Here now is a description of how the output from the comparators 233, 234 and 235 are logically combined to control the solenoid valve 204 and provide a signal to a recording device (not shown). Cross coupled NOR gates 238 and 239 form a set-reset (RS) flip-flop. This flip-flop will be reset when the fluid flow metering unit 209 is low on fluid (its displacement has been drawn out) and set when the refill operation has replaced that displacement (the fluid flow metering unit 209 is full of fluid).

To this end, the output of comparator 233 may be considered to be the R input to the flip-flop, while the Q output of the flip-flop may be considered to be the output of NOR gate 239. As fluid is withdrawn from the fluid flow metering unit 209, it flows downwards by gravity and suction out of expansion chamber 211. Eventually the last of the fluid will pass sensor A. While fluid was at sensor A the output from comparator 233 was near ground (logical zero). As the last of the fluid passes sensor A the output from comparator 233 switches to +6 V (logical one). This is an R input to the flip-flop, and forces the output of NOR gate 239 to 0V (low, or false). This condition represents the consumption of the displacement of the fluid flow metering unit 209. When the Q output is low it (ordinarily) produces a high (true) output from NOR gate 240. In turn, that turns on transistors 214, 242 and 243. This both increments the recording device (transistor 214) and activates the solenoid valve 204 (transistors 242 and 243) to refill the fluid flow metering unit 209.

Ordinarily, the RS flip-flop will remain reset for only a brief period of time, 1.6 to 3.0 seconds, and will become again set by actions described below. However, if the fluid reservoir 102 were to become empty, some means is needed to prevent continuous activation of the solenoid valve 204, and subsequent battery discharge. The triggering of timer 241 by the Q output going low is the needed mechanism. If the flip-flop stays reset for longer than the fifteen seconds allowed by the timer, the solenoid valve 204 is shut off and metering action is halted. This happens because, after fifteen seconds, the output of the timer 241 will go true, forcing the output of gate 240 low, overriding the fact that Q is low. And under the assumptions used, Q will not again go high, but will instead stay low (since no fluid is coming in→). Thus, the solenoid valve 204 is released and incrementing of the metering or recording device stops. Things are latched up until fluid is added and both sensors B and C can again sense the presence of fluid.

However, assuming instead that the fluid reservoir 102 is not empty, activating the solenoid valve 204 will indeed begin a refill of the fluid flow metering unit 209. Almost immediately fluid will again be detected by sensor A. That, however, merely returns the output of comparator 233 to low, and removes the R input to the flip-flop; it does not produce an S input to the flip-flop. That requires that fluid be present at both sensors B and C. When that condition is met both of comparators 234 and 235 will produce low outputs. As soon as that happens the output of NOR (operated as an AND) gate 237 will go high (true). This is the needed S input which resets the timer 241 and results in turning off transistors 214, 242 and 243. In turn, that releases the solenoid valve 204, and the cycle is complete.

The reason that the "full" condition is represented with two sensors B and C, instead of simply one (C), has to do with the potential mischief that might be caused by stray water drops (the potential "large bubble" problem mentioned earlier). The situation that is cured by two sensors B and C is one where the withdrawal of fluid might suck a drop at the open end 210 back into the region 305, and entrap a region of air (the "large bubble") in the process. It is not the entrapped air in and of itself that is the problem; afterall, it was properly there when the water drop got sucked in up past sensor C. Now, if the water drop got sucked in very early during the withdrawal, it might enter the expansion chamber 211 and simply join the other fluid being withdrawn. But suppose that the drop was sucked in fairly late in the withdrawal. Under these circumstances, the drop would be drawn in past sensor C, but not into the expansion chamber 211. Now let sensor A indicate that the fluid flow metering unit 209 is ready to be refilled. As the fluid comes in it pushes the air in the fluid flow metering unit 209 ahead of it, which in turn carries the water drop with it. When that water drop reaches sensor C it will appear to sensor C that the refill is complete, when in fact it is not. The net result is that the displacement of the fluid flow metering unit 209 has been reduced by the volume of air trapped therein by the sucked-in water drop.

The reason for having both sensors B and C, then, is this. They are spaced apart sufficiently far that no sucked-in drop can activate them both at once, nor can such a drop contribute to the formation of a true signal from AND gate 237. This latter assertion will indeed be true provided the volume of the expansion chamber 211 exceeds the volume of the tubing between sensors B and C. (That eliminates the case where the leading edge of the refill fluid trips sensor B while the drop trips sensor C.) All that happens with such a sucked-in drop now is that it is (harmlessly) expelled during the next refill operation.

If it were guaranteed that no drops could ever be sucked in the open end 210 as fluid is withdrawn (say, because the open end is flared or somehow else advantageously shaped), then the use of sensor B could be eliminated in favor of a two sensor design (sensors A and C only).

Finally, consider the advantage afforded by the use of a three-way solenoid valve 204. It might be thought that there is an economy to be realized by replacing the three-way solenoid valve 204 with a tee and then place a simple one-way solenoid valve in the line 208 leading to the fluid supply reservoir 102. It is not that this won't work. It will; however, it might not be as accurate unless certain difficulties are overcome. The chief difficulty is this. During evaporation there is some definite (although not any one particular) pressure distribution along tube 205, causing it to experience a corresponding change in volume, owing to its elasticity. If there were a tee and a one-way valve, then during refill that definite pressure distribution would abruptly be disturbed by application to the lower end of tube 205 of an above atmospheric pressure, namely, the head of water existing in the supply reservoir 102. This can cause expansion and contraction of supply tube 205, resulting in volume variations therein that contribute to the flow of fluid being evaporated, but that are not measured.

The three-way solenoid valve 204 avoids this difficulty through either a break-before-make mode of operation or by very rapid switching, and by having good isolation between switched fluid flow paths (i.e., it is "tight", and does not leak). Thus, the existing pressure distribution along tube 205 is largely maintained during the refill operation, so that there are no wide swings in fluid pressure in supply tube 205, and no changes in the volume therein. If tube 205 were rigid, then it might be desirable to replace the three-way solenoid valve with a tee and a one-way solenoid valve, as described above.

What is claimed is:

1. An atmometer comprising:
   an evaporator, having a fluid inlet, that evaporates a fluid whose evaporation is to be measured;
   a fluid supply that supplies fluid to be evaporated;
   a flow metering reservoir having a service orifice that receives, retains and subsequently supplies retained fluid, through the service orifice;
   a valve, hydraulically coupled to the fluid inlet of the evaporator, to the fluid supply and to the service orifice of the flow metering reservoir, that while in a first state (a) hydraulically couples the fluid inlet of the evaporator to the service orifice of the flow metering reservoir and (b) blocks fluid flow from the supply outlet of the fluid supply, and also that while in a second state (c) blocks fluid flow between the valve and the fluid inlet of the evaporator and also (d) hydraulically couples the supply outlet of the fluid supply to the service orifice of the flow metering reservoir;
   a fluid sensing circuit, disposed proximate the flow metering reservoir, that produces a first signal indicative of when the flow metering reservoir contains an amount of fluid less than or equal to a first selected amount and a second signal indicative of when the flow metering reservoir contains an amount of fluid greater than or equal to a second selected amount that is greater than the first selected amount; and
   a valve control circuit, coupled to the valve and responsive to the first and second signals, that causes the valve to be in the second state upon the presence of the first signal, to then remain in the second state until the presence of the second signal, to return to the first state upon the presence of the second signal, and to subsequently remain in the first state in the absence of both the first and second signals.

2. An atmometer as in claim 1 further comprising a recording signal output, coupled to the valve control circuit, that produces a cycle in a recording signal for each time the valve control circuit causes the valve to be in the second state.

3. An atmometer as in claim 1 further comprising a switch, coupled to the valve, for momentarily forcing the valve to be in the second state.

4. An atmometer as in claim 1 further comprising a timer, coupled to the valve control circuit, that forces the valve to return to the first state if the second state lasts longer than a preselected length of time.

5. An atmometer as in claim 1 wherein the fluid sensing circuit includes first, second and third fluid sensors and further wherein (a) the second and third fluid sensors are disposed a first distance apart along a generally cylindrical portion of the flow metering reservoir distally removed from the service orifice, and (b) the second signal is derived from the logical conjunction of the second and third fluid sensors.

6. An atmometer as in claim 5 wherein the flow metering reservoir includes an expansion chamber.

7. An atmometer as in claim 6 wherein the interior volume of the expansion chamber is greater than the interior volume of the generally cylindrical portion of the flow metering reservoir that lies between the second and third fluid sensors.

8. An atmometer as recited in claim 1 wherein the flow metering reservoir further includes a vent open to the atmosphere.

9. An atmometer as in claim 8 wherein the fluid sensing circuit includes first, second and third fluid sensors and further wherein (a) the second and third fluid sensors are disposed proximate the vent and a first distance apart along a generally cylindrical portion of the flow metering reservoir, and (b) the second signal is derived from the logical conjunction of the second and third fluid sensors.

10. An atmometer as recited in claim 1 wherein the fluid sensing circuit comprises a radio frequency oscillator, a detector of radio frequency voltage, and a capacitive path therebetween whose dielectric constant varies according to the presence or absence of fluid proximate the capacitive path.

11. An atmometer comprising:
    an evaporator, having a fluid inlet, that evaporates a fluid whose evaporation is to be measured;
    a fluid supply that supplies fluid to be evaporated;
    a flow metering reservoir having a service orifice that receives, retains and subsequently supplies retained fluid, through the service orifice;
    a valve, hydraulically coupled on one side to the fluid supply and on an opposite side via a tee connection to the service orifice of the flow metering reservoir and to the fluid inlet of the evaporator, that while in a first state blocks fluid flow from the fluid supply, and also that while in a second state hydraulically couples the fluid supply to the service orifice of the flow metering reservoir;

a fluid sensing circuit, disposed proximate the flow metering reservoir, that produces a first signal indicative of when the flow metering reservoir contains an amount of fluid less than or equal to a first selected amount and a second signal indicative of when the flow metering reservoir contains an amount of fluid greater than or equal to a second selected amount that is greater than the first selected amount;

a valve control circuit, coupled to the valve and responsive to the first and second signals, for causing the valve to be in the second state upon the presence of the first signal, to then remain in the second state until the presence of the second signal, to return to the first state upon the presence of the second signal, and to subsequently remain in the first state in the absence of both the first and second signals; and a timer, coupled to the valve control circuit, that forces the valve to return to the first state if the second state lasts longer than a preselected length of time.

12. An atmometer comprising:

an evaporator, having a fluid inlet, that evaporates a fluid whose evaporation is to be measured;

a fluid supply that supplies fluid to be evaporated;

a flow metering reservoir having a service orifice that receives, retains and subsequently supplies retained fluid, through the service orifice;

a valve, hydraulically coupled on one side to the fluid supply and on an opposite side via a tee connection to the service orifice of the flow metering reservoir and to the fluid inlet of the evaporator, that while in a first state blocks fluid flow from the fluid supply, and also that while in a second state hydraulically couples the fluid supply to the service orifice of the flow metering reservoir;

a fluid sensing circuit, disposed proximate the flow metering reservoir, that produces a first signal indicative of when the flow metering reservoir contains an amount of fluid less than or equal to a first selected amount and a second signal indicative of when the flow metering reservoir contains an amount of fluid greater than or equal to a second selected amount that is greater than the first selected amount;

a valve control circuit, coupled to the valve and responsive to the first and second signals, for causing the valve to be in the second state upon the presence of the first signal, to then remain in the second state until the presence of the second signal, to return to the first state upon the presence of the second signal, and to subsequently remain in the first state in the absence of both the first and second signals; and wherein the fluid sensing circuit includes first, second and third fluid sensors and further wherein (a) the second and third fluid sensors are disposed a first distance apart along a generally cylindrical portion of the flow metering reservoir distally removed from the service orifice, and (b) the second signal is derived from the logical conjunction of the second and third fluid sensors.

13. An atmometer as in claim 12 wherein flow metering reservoir includes an expansion chamber.

14. An atmometer as in claim 13 wherein the interior volume of the expansion chamber is greater than the interior volume of the generally cylindrical portion of the flow metering reservoir that lies between the second and third fluid sensors.

15. An atmometer comprising:

an evaporator, having a fluid inlet, that evaporates a fluid whose evaporation is to be measured;

a fluid supply that supplies fluid to be evaporated;

a flow metering reservoir having a service orifice that receives, retains and subsequently supplies retained fluid, through the service orifice;

a valve, hydraulically coupled on one side to the fluid supply and on an opposite side via a tee connection to the service orifice of the flow metering reservoir and to the fluid inlet of the evaporator, that while in a first state blocks fluid flow from the fluid supply, and also that while in a second state hydraulically couples the fluid supply to the service orifice of the flow metering reservoir;

a fluid sensing circuit, disposed proximate the flow metering reservoir, that produces a first signal indicative of when the flow metering reservoir contains an amount of fluid less than or equal to a first selected amount and a second signal indicative of when the flow metering reservoir contains an amount of fluid greater than or equal to a second selected amount that is greater than the first selected amount;

a valve control circuit, coupled to the valve and responsive to the first and second signals, for causing the valve to be in the second state upon the presence of the first signal, to then remain in the second state until the presence of the second signal, to return to the first state upon the presence of the second signal, and to subsequently remain in the first state in the absence of both the first and second signals; and wherein the flow metering reservoir includes a vent open to the atmosphere, wherein the fluid sensing circuit includes first, second and third fluid sensors and further wherein (a) the second and third fluid sensors are disposed proximate the vent and a first distance apart along a generally cylindrical portion of the flow metering reservoir, and (b) the second signal is derived from the logical conjunction of the second and third fluid sensors.

* * * * *